United States Patent
Nissels

[11] Patent Number: 6,126,628
[45] Date of Patent: Oct. 3, 2000

[54] FLUID FLOW LIMITING DEVICE

[75] Inventor: Robert Nissels, Corbeyrier, Switzerland

[73] Assignee: Johnson & Johnson Professional, Inc., Raynham, Mass.

[21] Appl. No.: 08/837,665

[22] Filed: Apr. 22, 1997

[51] Int. Cl.[7] .................................................. A61M 5/00
[52] U.S. Cl. ....................................... 604/9; 604/8
[58] Field of Search .................... 604/8–10, 247, 604/65; 137/109, 110, 505.13, 512.1

[56] References Cited

U.S. PATENT DOCUMENTS

| | | | |
|---|---|---|---|
| 3,444,861 | 5/1969 | Schulte | 128/350 |
| 3,492,996 | 2/1970 | Fountain | 128/350 |
| 3,886,948 | 6/1975 | Hakim | 128/350 |
| 4,206,761 | 6/1980 | Cosman | 128/660 |
| 4,206,762 | 6/1980 | Cosman | 128/660 |
| 4,281,666 | 8/1981 | Cosman | 128/748 |
| 4,281,667 | 8/1981 | Cosman | 128/748 |
| 4,332,255 | 6/1982 | Hakim et al. | 128/350 |
| 4,382,445 | 5/1983 | Sommers | 604/8 |
| 4,387,715 | 6/1983 | Hakim et al. | 604/9 |
| 4,443,214 | 4/1984 | Marion | 604/9 |
| 4,475,898 | 10/1984 | Brodner et al. | 604/9 |
| 4,551,128 | 11/1985 | Hakim et al. | 604/9 |
| 4,578,057 | 3/1986 | Sussman | 604/9 |
| 4,583,967 | 4/1986 | Harris | 604/9 |
| 4,589,287 | 5/1986 | Dickens | 73/727 |
| 4,595,390 | 6/1986 | Hakim et al. | 604/9 |
| 4,605,395 | 8/1986 | Rose et al. | 604/9 |
| 4,615,691 | 10/1986 | Hakim et al. | 604/9 |
| 4,621,654 | 11/1986 | Holter | 137/38 |
| 4,631,051 | 12/1986 | Harris | 604/9 |
| 4,653,508 | 3/1987 | Cosman | 128/748 |
| 4,660,568 | 4/1987 | Cosman | 128/748 |
| 4,673,384 | 6/1987 | Marion | 604/10 |
| 4,681,559 | 7/1987 | Hooven | 604/9 |
| 4,741,730 | 5/1988 | Dormandy, Jr. et al. | 604/8 |
| 4,772,257 | 9/1988 | Hakim et al. | 604/9 |
| 4,781,673 | 11/1988 | Watanabe | 604/9 |
| 4,784,638 | 11/1988 | Ghajar | 604/49 |
| 4,787,886 | 11/1988 | Cosman | 604/9 |
| 4,787,887 | 11/1988 | Saenz Arroyo | 604/9 |
| 4,861,331 | 8/1989 | East et al. | 604/9 |
| 4,885,002 | 12/1989 | Watanabe et al. | 606/9 |
| 4,931,039 | 6/1990 | Coe et al. | 604/53 |
| 5,000,731 | 3/1991 | Wong et al. | 604/8 |
| 5,054,518 | 10/1991 | Rancani | 137/516.27 |
| 5,069,663 | 12/1991 | Sussman | 604/9 |
| 5,096,004 | 3/1992 | Ide | 175/107 |
| 5,098,411 | 3/1992 | Watson et al. | 604/268 |
| 5,112,304 | 5/1992 | Barlow et al. | 604/96 |
| 5,154,693 | 10/1992 | East et al. | 604/9 |
| 5,167,615 | 12/1992 | East et al. | 604/9 |
| 5,176,627 | 1/1993 | Watson | 604/8 |
| 5,207,684 | 5/1993 | Nobles | 606/108 |
| 5,257,630 | 11/1993 | Broitman et al. | 128/675 |
| 5,304,114 | 4/1994 | Cosman et al. | 604/8 |
| 5,325,865 | 7/1994 | Beckman et al. | 128/748 |

(List continued on next page.)

*Primary Examiner*—John G. Weiss
*Assistant Examiner*—William Noggle
*Attorney, Agent, or Firm*—Nutter, McClennen & Fish LLP

[57] ABSTRACT

A device for limiting the flow of a fluid from a first region of a patient's body to a second region includes a primary passage for directing fluid from an inlet of the device to an outlet in response to the fluid flow rate being less than a predetermined level and a secondary passage for directing fluid from the inlet to the outlet in response to the flow rate being greater than or equal to the predetermined level. The secondary passage can be characterized as a tortuous flow path and presents a higher resistance to fluid flow than the primary passage. A detector is operative to close the primary passage in response to the flow rate reaching the predetermined level in order to force the fluid to pass through the secondary passage. With this arrangement, when the fluid flow rate reaches a level characteristic of overdrainage, the fluid is forced through the secondary passage in order to effectively reduce the fluid flow rate and prevent overdrainage. As soon as the flow rate decreases below the predetermined level, the primary passage opens itself automatically.

12 Claims, 10 Drawing Sheets

U.S. PATENT DOCUMENTS

| | | | |
|---|---|---|---|
| 5,336,166 | 8/1994 | Sierra | 604/9 |
| 5,368,556 | 11/1994 | Lecuyer | 604/8 |
| 5,405,316 | 4/1995 | Magram | 604/8 |
| 5,437,627 | 8/1995 | Lecuyer | 604/9 |
| 5,464,144 | 11/1995 | Guy et al. | 227/176 |
| 5,497,934 | 3/1996 | Brady et al. | 227/176.1 |
| 5,503,320 | 4/1996 | Webster et al. | 227/176.1 |
| 5,531,673 | 7/1996 | Helenowski | 604/9 |
| 5,584,314 | 12/1996 | Bron | 137/239 |
| 5,628,755 | 5/1997 | Heller | 606/108 |
| 5,634,894 | 6/1997 | Magram | 604/10 |
| 5,643,195 | 7/1997 | Drevet | 604/9 |
| 5,660,200 | 8/1997 | Paes | 137/110 |

FLUID FLOW LIMITING DEVICE

CROSS REFERENCE TO RELATED APPLICATIONS

Not Applicable.

STATEMENTS REGARDING FEDERALLY SPONSORED RESEARCH

Not Applicable.

BACKGROUND OF THE INVENTION

Shunt systems for directing body fluid from one region to another are known in the medical field. One application for such a fluid shunt system is in the treatment of hydrocephalus in order to direct cerebrospinal fluid away from the brain and into the venous system or to another region of the body. In this application, a shunt is implanted on the patient's skull, under the scalp, and is coupled to a brain ventricle catheter which is adapted for insertion into the brain and to a distal catheter which is adapted for insertion into the drainage region, such as the peritoneal cavity, the atrium or other drainage site.

Generally, fluid shunt systems include a valve mechanism for controlling, or regulating the fluid flow rate. Illustrative valve mechanisms operate to permit fluid flow only once the fluid pressure reaches a certain level and may permit adjustment of the pressure level at which fluid flow commences.

One such adjustable valve, described in U.S. Pat. No. 4,551,128 (Hakim et al.), includes a flexible diaphragm and plate positioned to divide a housing into inlet and outlet chambers which communicate through an aperture in the plate. A valve element is biased against the aperture to close the aperture until the fluid pressure in the inlet chamber exceeds a preselected "popping pressure." The popping pressure is adjustable by adjusting an external screw of the valve. However, due to the elastomeric properties of the diaphragm material, maintenance of the implanted valve may be required. Further, flow rate adjustment of the Hakim et al. device after implantation may require a surgical procedure.

Another adjustable valve mechanism, described in U.S. Pat. No. 4,781,673 (Watanabe), includes two parallel fluid flow passages, with each passage including a flow rate regulator and an on-off valve. Fluid flow through the passages is manually controlled by palpably actuating the on-off valves through the scalp. Although the Watanabe device permits flow rate control palpably through the scalp and thus, without surgical intervention, patient and/or physician attention to the valve settings is required.

Effective fluid flow rate control is particularly important since overdrainage of cerebrospinal fluid can result in dangerous conditions, including subdural hematoma. Overdrainage tends to occur when a patient moves from a horizontal position to a sitting or standing position, due to a siphon effect in the shunt system. In order to reduce the risk of overdrainage, some shunt systems include additional devices, sometimes referred to as anti-siphon devices, for preventing overdrainage. Some such devices use weights, which move in response to the patient changing position, to open or close the fluid flow path. One system, described in U.S. Pat. No. 5,368,556 (Lecuyer), includes spherical weights which provide additional compressive force against a valve spring to help maintain the valve in a closed position when the patient is sitting or standing. However, noise associated with the use of such weights may be objectionable.

SUMMARY OF THE INVENTION

The invention relates to a fluid flow limiting device for use with a shunt system. The device includes an inlet for receiving fluid from a first region of a patient's body into the device, an outlet for directing the fluid from the device, and two fluid passages, or flow paths. A primary fluid passage directs fluid from the inlet to the outlet substantially directly in response to the flow rate being less than a predetermined level. A secondary fluid passage directs fluid from the inlet to the outlet in response to the flow rate being greater than the predetermined level. Preferably, the secondary passage is tortuous so as to present a higher resistance to fluid flow than the primary passage. A detector is operable to close the primary passage when the flow rate reaches the predetermined level in order to force the fluid to pass through the secondary passage. As soon as the flow rate decreases below the predetermined level, the primary passage opens automatically.

With this arrangement, when the fluid flow rate is less than a predetermined level characteristic of overdrainage, most of the fluid flows through the substantially direct primary passage since the secondary passage presents a higher resistance. When the fluid flow rate reaches the predetermined level, the fluid is forced to flow through the secondary passage which serves effectively to reduce the flow rate through the device and prevent overdrainage. Further, the device advantageously prevents overdrainage in response to the increased fluid flow rates without the need for manual intervention and with a rigid structure that is not susceptible to occlusion by the application of normal external forces. The fluid flow limiting device is suitable for use as a separate device in series with a valve component of the shunt system, or it can be readily incorporated into a drainage system along with the valve component.

In one embodiment, the overdrainage protection device includes a housing defining the inlet, a body disposed at least partially within the housing and having a body channel terminating at the outlet, a detector disposed between the inlet and the body channel and a flow reducing element. The detector includes a detector channel in substantial axial alignment with the body channel to form the primary passage and the flow reducing element is disposed between the body and the housing to form the secondary passage. In one embodiment, the flow reducing element includes a helical passageway. Many other passageway configurations may also be used.

One illustrative detector includes a detector seat having an aperture and a closure element that is moveable between a first position in spaced relation with the detector seat in which the primary passage is open and a second position abutting the detector seat to block the aperture and close the primary passage. Preferably, the closure element is biased into spaced relation with the detector seat in order to expose the aperture and open the primary passage. In one embodiment, a first bias element urges the closure element away from the detector seat to maintain the primary passage in an open position. The force of the first bias element is at least partially opposed by a counterbias element which urges the closure element back towards the detector seat. The force of the first bias element preferably exceeds that of the counterbias element so that, in normal operation, without an excessive rate of fluid flow, the primary passage is open.

The invention also provides a method for limiting fluid flow through a device having an inlet, an outlet, a primary flow path between the inlet and the outlet and a secondary flow path between the inlet and the outlet. The method includes the steps of directing the fluid through the primary passage of the device in response to the fluid flow rate being less than a predetermined level and directing the fluid through a secondary passage in response to the fluid flow rate reaching or exceeding the predetermined level. The primary passage is closed, such as with the use of a detector, when the fluid flow rate reaches the predetermined level in order to force the fluid to pass through the secondary passage. In one embodiment, the step of directing the fluid through the secondary passage includes directing the fluid through a passageway of a desired configuration, as may be provided by the threads of a screw element. The secondary passage can include multiple adjacent helical passageways.

DETAILED DESCRIPTION OF THE INVENTION

The fluid flow limiting device of the present invention, which is described in detail below, is suitable for implanting into a patient to limit the flow of a body fluid from a first region to a second region. The illustrated devices limit the flow of cerebrospinal fluid from the brain of a patient to a drainage system or region, such as the peritoneal region. However, it will be appreciated by those of ordinary skill in the art that the concepts and techniques described herein are suitable for use in other applications in which it is desired to limit the flow of a fluid from one region of a patient to another.

In general, the fluid flow limiting device includes an inlet for receiving fluid from the brain into the device and an outlet for directing fluid from the device to the drainage region (e.g., peritoneal cavity, atrium). The device is intended for use with a shunt system including a valve for controlling flow rate and various placements of the fluid flow limiting device relative to the shunt system are possible.

Figure 1:
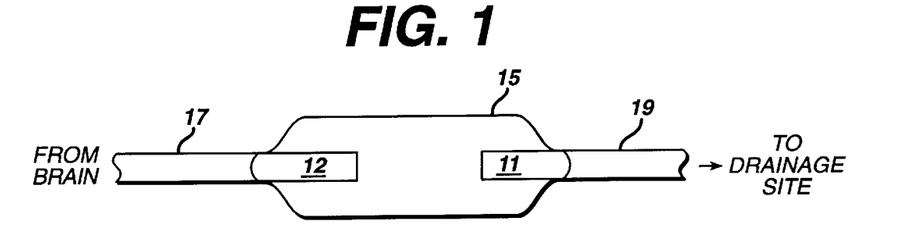
FIG. 1 illustrates placement of a fluid flow limiting device of the invention relative to a fluid shunt system disposed in a patient.
Figure 1A:
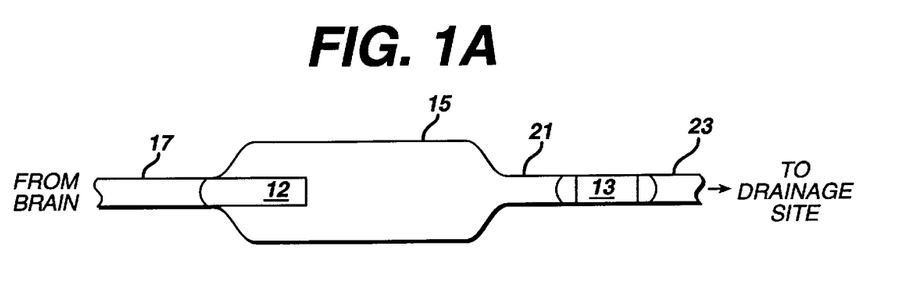
FIG. 1A illustrates an alternate placement of a fluid flow limiting device of the invention relative to a fluid shunt system disposed in a patient.

Referring to FIG. 1, the fluid flow limiting device 11 may be disposed in an entourage 15 of the shunt system, along with the valve 12. A first end of the entourage 15 is adapted for coupling to the patient's brain via an inlet tube 17 and a second end of the entourage is adapted for coupling to the drainage site via an outlet tube 19. Referring to FIG. 1A, the fluid flow limiting device 13 may alternatively be disposed in line with the entourage 15, between a first outlet tube 21 and a second outlet tube 23, as shown.

Figure 2:
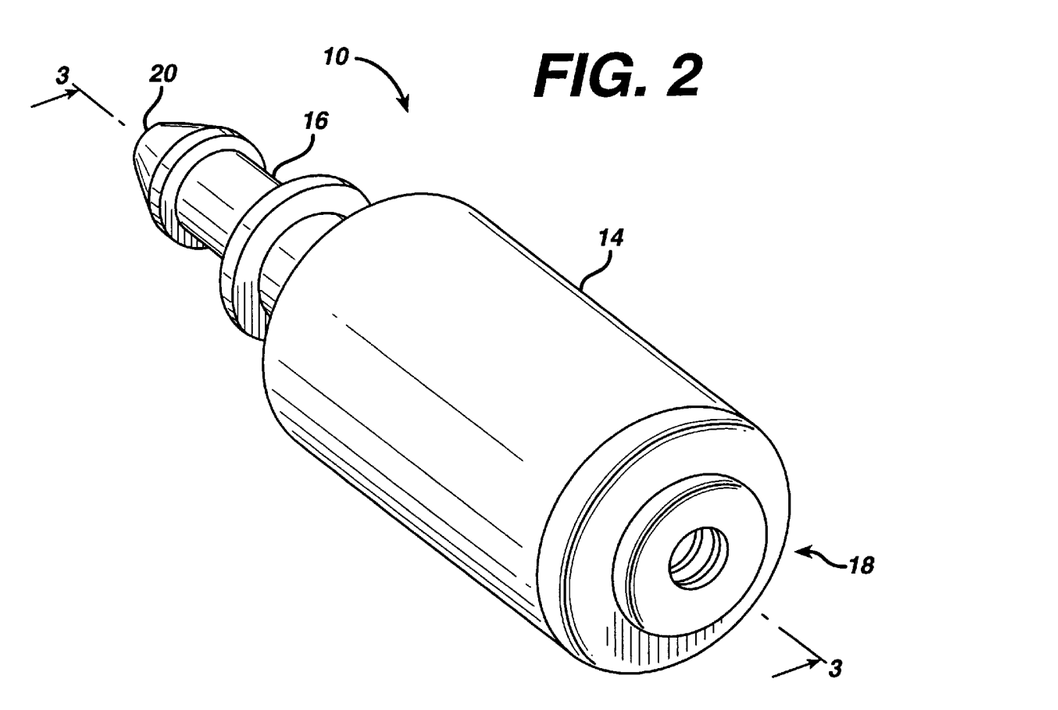
FIG. 2 is an isometric view of a fluid flow limiting device in accordance with the invention.
Figure 3:
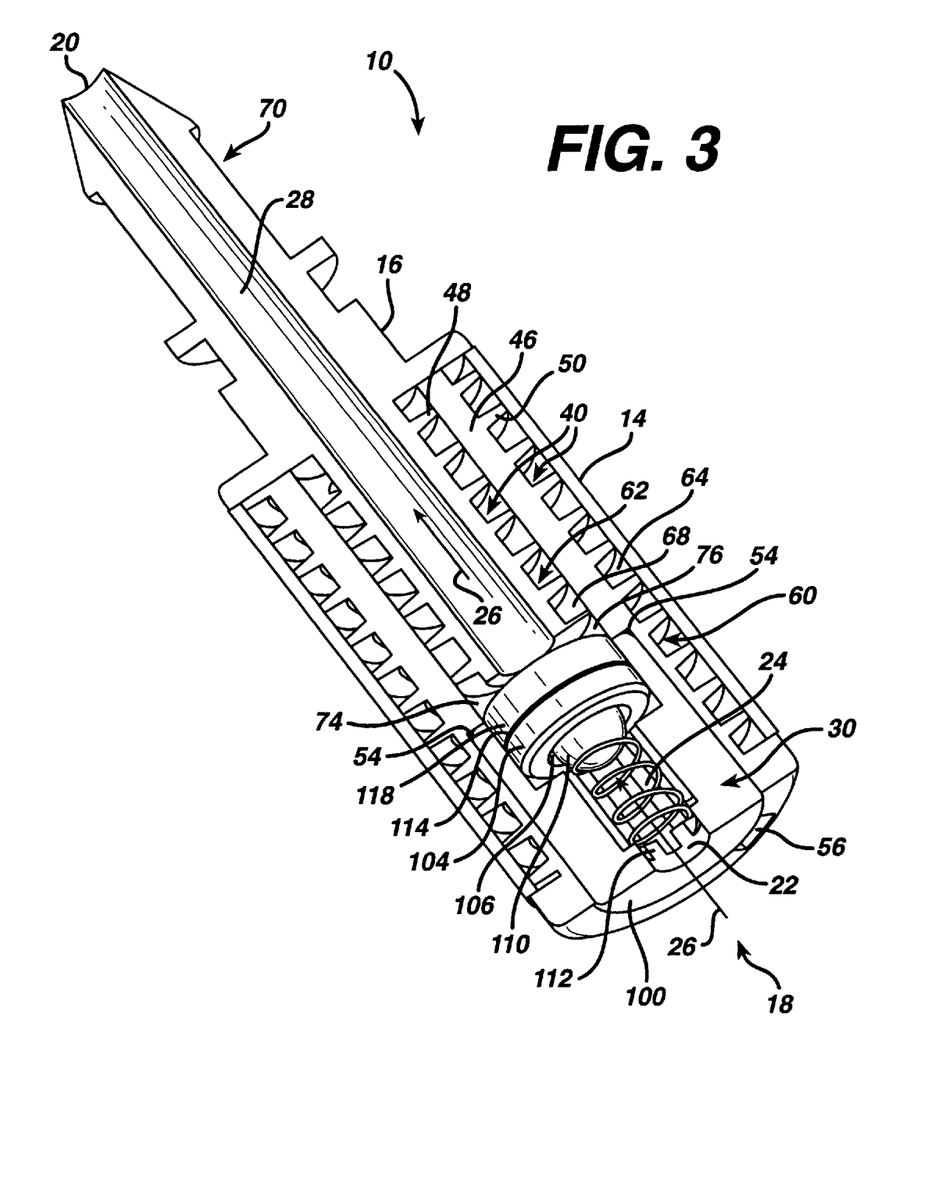
FIG. 3 is a cross-sectional isometric view of the fluid flow limiting device of FIG. 2 taken along line 3—3 of FIG. 2.

Referring to FIGS. 2 and 3, a fluid flow limiting device 10 according to the invention is shown. The device 10 is intended for placement in an entourage, like device 11 of FIG. 1. To this end, device 10 includes an inlet 18 in the form of an aperture disposed in the entourage and an outlet 20 in the form of a connector 70 suitable for coupling to a drainage catheter (i.e., outlet tube 19 in FIG. 1).

The device 10 includes a housing 14 defining the inlet 18 at the proximal end of the device. A device body 16 defines the outlet 20 at the distal end of the device through which the fluid is directed from the device. At least a portion of the device body 16 is disposed in the housing 14, as shown. The components of the device 10, including the housing 14 and body 16, are fabricated with any suitable biocompatible material. Examples of such preferred materials include polyethersulfone (PES), polysulfone (PS), polyurethane, polyethylene and polypropylene.

Figure 4:
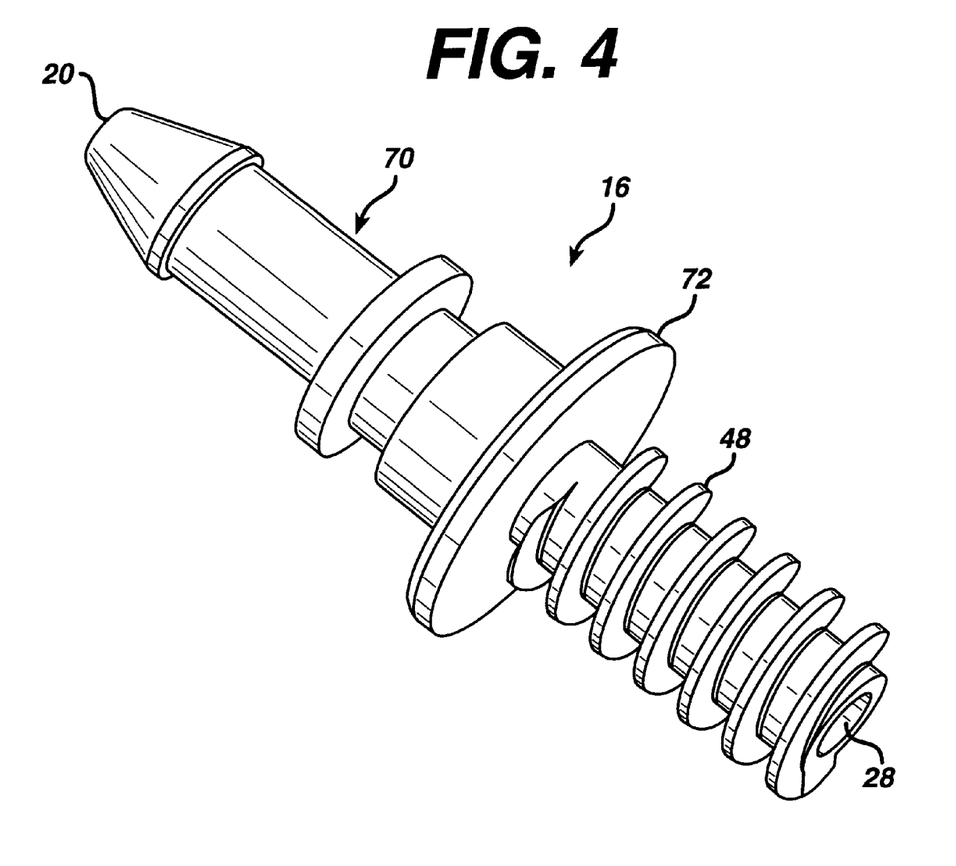
FIG. 4 is an isometric view of the body of the fluid flow limiting device of FIG. 2.

Referring to FIG. 4, the device body 16 includes the outlet connector 70, a plurality of external screw threads, or helical vanes 48 and a longitudinal channel, referred to as the body channel 28 which extends along a direct path from a proximal end of the body to the distal end. A flange 72 separates the outlet connector 70 from the threads 48, as shown.

A detector 30 (FIG. 3), referred to alternatively as a valve element, is disposed within the housing 14 in substantial axial alignment with the body channel 28. The detector 30 includes a detector channel 24 extending from an aperture 22 of the inlet 18 to the body channel 28, a detector seat 104 having an aperture 106 and a closure element 110. The closure element 110 is moveable between a first position away from and in spaced relation to the detector seat 104 to expose the aperture and open the channel 24 and a second position in abutment with the detector seat 104 to block the aperture 106 and close the channel 24. The detector 30 preferably has a bias element 114 that urges the closure element 110 away from the detector seat 104 to maintain channel 24 in an open position. The force of bias element 114 is at least partially opposed by counterbias element 112 which urges the closure element back towards detector seat 104. The force of bias element 114 preferably exceeds that of counterbias element 112 so that, in normal operation, without an excessive rate of fluid flow, channel 24 is open.

In the illustrative embodiment, the detector seat 104 includes a substantially circular aperture 106 and the closure element 110 is a substantially spherical ball. The counterbias element 112 and bias element 114 can be any suitable material or structure able to direct a force of a predetermined magnitude in one direction. In one embodiment, counterbias element 112 is a spring element, such as a coil spring and the bias element 114 is a flat spring. A fixation ring 118 positioned under the detector seat 104 maintains the flat spring 114 in contact with the detector seat 104. Suitable materials for fabricating the ball 110 and seat 104 include synthetic ruby (aluminum oxide), suitable materials for fabricating the detector components are the same as described above for the housing 14 and body 16 and suitable materials for fabricating the bias elements 112 and 114 include stainless steel (ASTM 300 Series, 316, 308, 304 and preferably, 316L).

The counterbias and bias elements 112 and 114 are designed to bias the closure element 110 relative to the detector seat 104 in order to provide a desired fluid flow rate through the channel 24. It will be appreciated by those of ordinary skill in the art that both the particular design of the springs, as well as their dimensions (e.g., thickness) and the material from which they are made, determine the relative "stiffness" of the springs and the resulting bias on the closure element 110. Flow rate can be controlled, at least in part, by altering the structure and/or design of elements 112, 114 or changing the relative position of the parts 118, 114 and 104 in the detector body 30.

Figure 5:
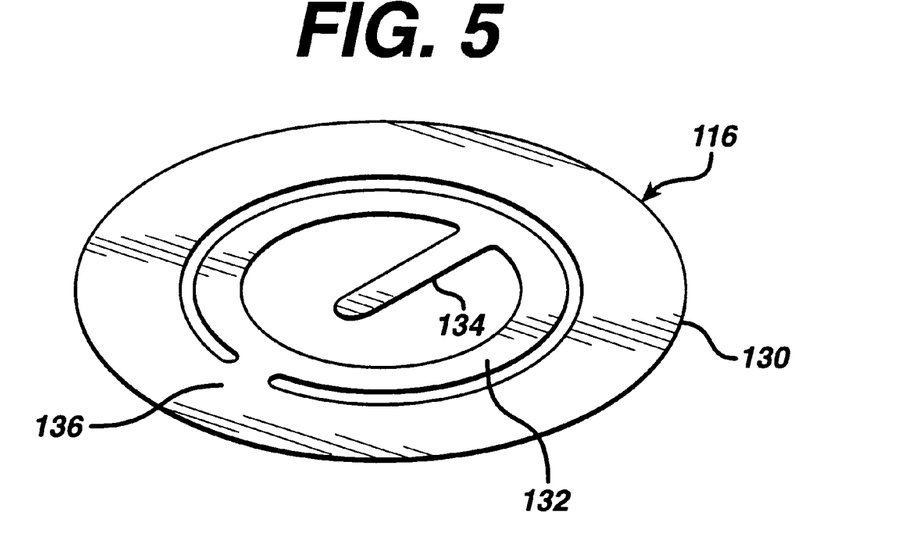
FIG. 5 illustrates a flat spring for use with the fluid flow limiting device of FIG. 2.

Referring also to FIGS. 5 and 6, two illustrative flat springs for use in providing the bias element 114 are shown. The flat spring 116 of FIG. 5 includes an exterior ring 130 and an interior ring 132 attached to the exterior ring by a connection member 136. A finger 134 is cantilevered inwardly from the interior ring 132 at a location opposite to the connection member 136, as shown. In assembly, the exterior ring 130 is pressed by the fixation ring 118 against the detector seat 104 and the interior ring 132 and the finger 134 are in contact with the closure element 110 so as to bias the closure element 110 away from the seat 104. The design of the spring 116 advantageously avoids impeding the flow of fluid through the detector channel 24.

Figure 6:
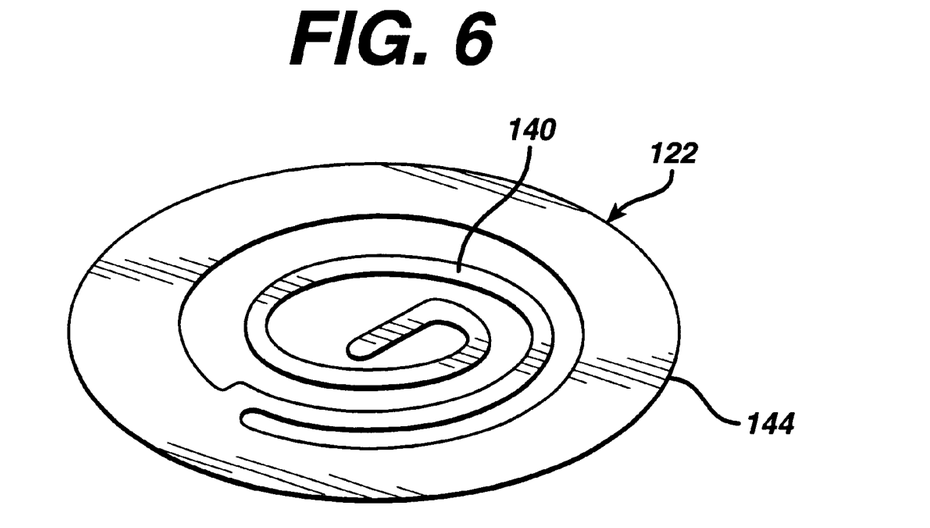
FIG. 6 illustrates an alternate flat spring for use with the fluid flow limiting device of FIG. 2.

The flat spring 122 of FIG. 6 includes a spiral member 140 attached to an exterior ring 144, as shown. In assembly, the exterior ring 144 is pressed against the detector seat 104 by the fixation ring 118 and the spiral member 140 contacts the closure element 110 so as to bias the closure element 110 away from the detector seat 104. The design of the flat spring 122 of FIG. 6 provides reduced stiffness for the same thickness of material, as compared to the spring 116 of FIG. 5.

A first, or primary fluid flow path, or passage 26 (FIG. 3) in fluid communication with the inlet 18 and the outlet 20 includes the detector channel 24 and the substantially axially aligned body channel 28. In normal operation, without an excessive rate of fluid flow, fluid flows directly from the inlet 18 to the outlet 20 through the primary passage 26.

A flow reducing element 46 (FIG. 3) is disposed between the housing 14 and the body 16 to form a secondary fluid passage 40 between the inlet 18 and the outlet 20 through which fluid is directed in response to the fluid flow rate reaching and/or exceeding the predetermined level, as will be described. Preferably, the secondary passage 40 can be characterized as a tortuous path and presents a higher resistance to fluid flow than does the primary passage 26. More particularly, the secondary passage 40 is tortuous in the sense that it includes twists, bends, turns, obstructions, or some combination thereof, and a combination of the length and design of the secondary passage results in a reduced fluid flow rate as compared to fluid flow through the primary passage 26. Shear and other forces create drag on the fluid as it passes through the secondary passage 40, reducing the flow rate.

In the illustrative embodiment, the flow reducing element 46 is in the form of a screw element 46 disposed concentrically between the body threads 48 and the housing 14, as shown. The screw element 46 has an inner surface 68 and a plurality of exterior helical vanes, or threads 50. In assembly, the screw threads 50 abut the inner surface 64 of the housing 14 in a fluid tight seal to form a first channel 60 of the secondary passage 40. Further, the body threads 48 abut the inner surface 68 of the screw element 46 in a fluid tight seal to form a second channel 62 of the secondary passage 40.

Figure 7:
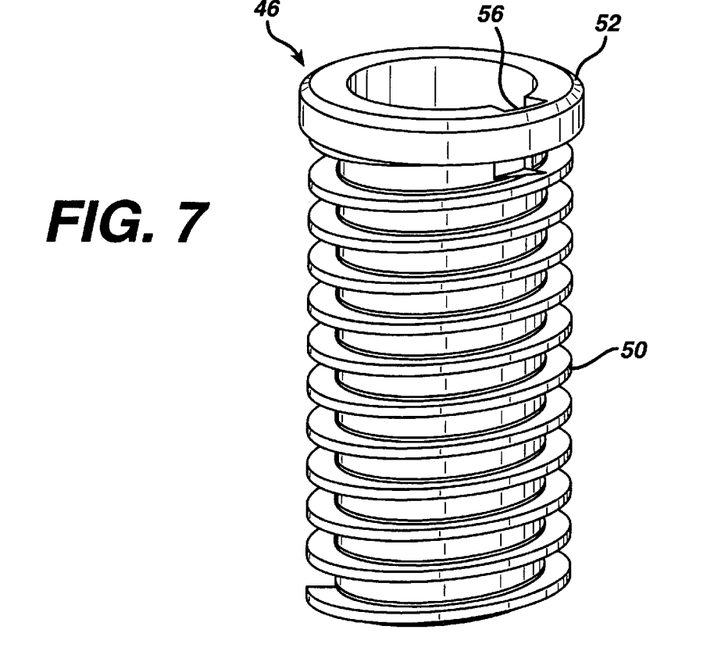
FIG. 7 is a view of the screw element of the fluid flow limiting device of FIG. 2.
Figure 7A:
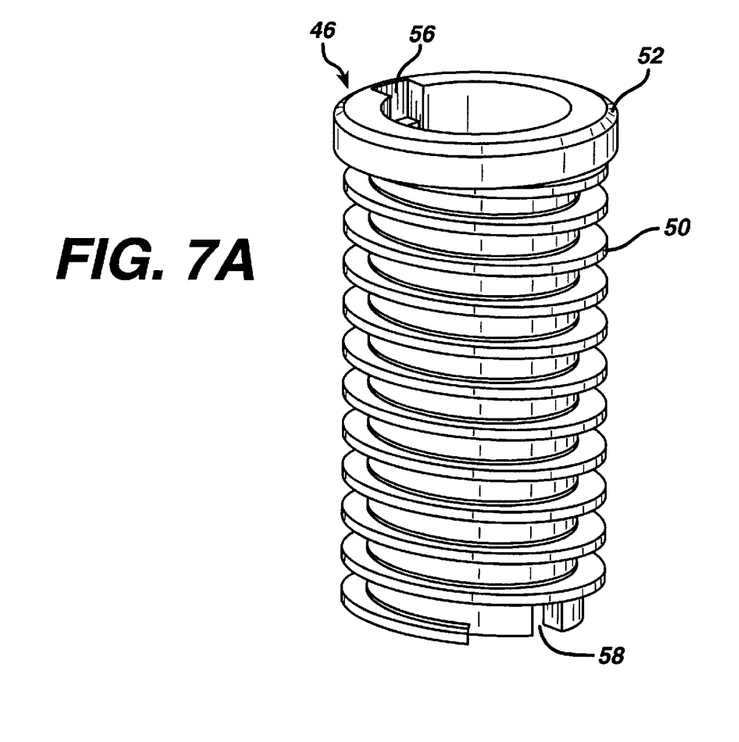
FIG. 7A shows the screw element of FIG. 7 rotated by 180 degrees.

Referring also to FIGS. 7 and 7A, two views of the screw element 46 are shown. The screw 46 has a flange 52 at a proximal end and a pair of slots 56, 58. A first one of the slots 56 is disposed at the proximal end of the screw element and extends longitudinally slightly beyond the flange 52, as is apparent from FIG. 7. The second slot 58 is disposed at the distal end of the screw 46, as shown. Slot 56 provides fluid communication between the inlet 18 and the channel 60 and slot 58 provides fluid communication between the channel 60 and the channel 62, as will be described. Thus, in the illustrative embodiment, the inlet 18 includes the screw slot 56 in fluid communication with the secondary passage 40 and the detector aperture 22 in fluid communication with the primary passage 26. In the illustrative embodiment, the threads 48 and 50 have a pitch of between approximately 1° to 40° and, preferably approximately 30°.

In assembly, the screw element 46 is positioned within the housing 14, with the screw flange 52 adjacent to the proximal end of the housing 14. The body 16 is inserted into the screw 46, with the body flange 72 adjacent to the distal end of the screw element 46 and the housing 14, as shown. The detector 30 is sized and shaped to fit within the screw element 46, in substantial axial alignment with the body 16. Ledges 54 on the inner surface 68 of the screw element 46 maintain alignment of the detector 30 and the body 16.

In operation, the springs 112 and 114 are provided with a stiffness suitable to bias the closure ball 110 into spaced relation with the detector seat 104 when the fluid flow rate through the detector 30 is less than a predetermined level, such as between approximately 25 to 100 ml/hour, and, more preferably, between approximately 30 to 60 ml/hour. It will be appreciated by those of ordinary skill in the art that flow rate is a function of the fluid pressure and velocity and thus, the predetermined fluid flow rate corresponds to a predetermined fluid pressure and velocity. With the valve 30 in the open position, fluid enters the inlet aperture 22 and travels through the primary passage 26. Note that some fluid will also enter the secondary passage 40 through the slot 56. However, since the secondary passage 40 presents a higher resistance to fluid flow than the primary passage 26, most of the fluid will flow through the primary passage 26. More particularly, in the primary passage 26 the fluid travels directly through the detector channel 24 and the body channel 28 to the outlet 20.

Once the flow rate of fluid entering the inlet aperture 22 reaches the predetermined level, the pressure on the closure element 110 exceeds the biasing force exerted by bias element 114. Preferably, the detector 30 is oriented so that, as the patient moves to a sitting or standing position, gravity acts in the same direction as the counterbias element 112, further forcing the ball 110 towards the seat 104. Under these conditions, the ball 110 is pushed into abutment with the detector seat 104, blocking the aperture 106 and closing the fluid channel 24 through the detector 30.

With the detector channel 24 and primary passage 26 effectively blocked, the fluid is forced to flow through the inlet slot 56 and into the secondary passage 40. More particularly, the fluid flows along the channel 60 in a substantially helical pattern between the screw threads 50 and the housing 14. Once the fluid reaches the distal end of the channel 60, the fluid enters the channel 62 via the screw slot 58 (FIG. 7A) and travels between the body threads 48 and the inner surface 54 of the screw element 46. At the end of channel 62, the fluid enters the primary passage 26 at an intermediate location 76, between the detector 30 and the body channel 24. That is, the body 16 is spaced from the detector 30 by a slot 74 through which the fluid enters the body channel 28 where it is directed to the outlet 20. Thus, in the device 10, fluid flow through the secondary passage 40 can be characterized as axially bi-directional since fluid travels along the device axis directed by screw threads 50 in a first direction and then by body threads 48 in a second direction.

With this arrangement, when the fluid flow rate reaches a level characteristic of overdrainage, the lower resistance path from the inlet 18 to the outlet 20 via the primary passage 26 is blocked by the detector 30 and the fluid is forced to flow through the tortuous secondary passage 40. In this way, the flow rate of fluid flowing between the inlet 18 and the outlet 20 is effectively reduced and overdrainage is prevented. Once the fluid flow decreases below the predetermined level, the force of the bias element 114 exceeds that of the counterbias element 112, thereby causing the primary passage 26 to automatically open.

Figure 8:
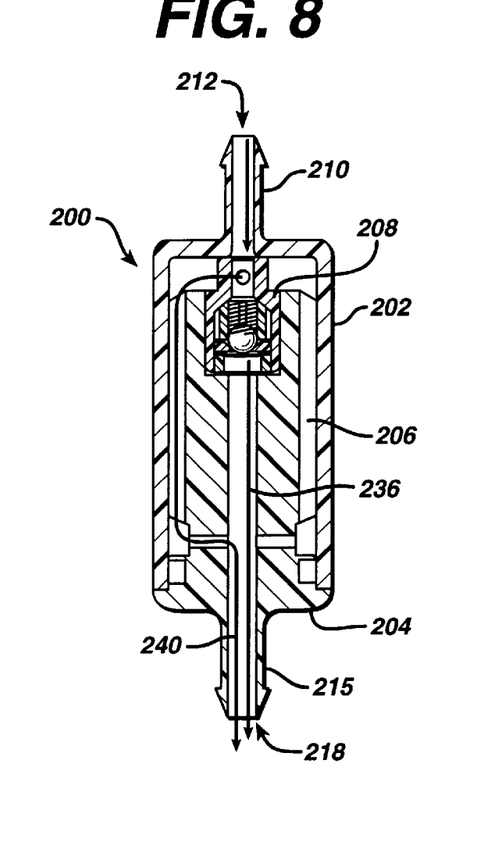
FIG. 8 is a cross-sectional view of an alternate embodiment of a fluid flow limiting device in accordance with the invention.
Figure 10:
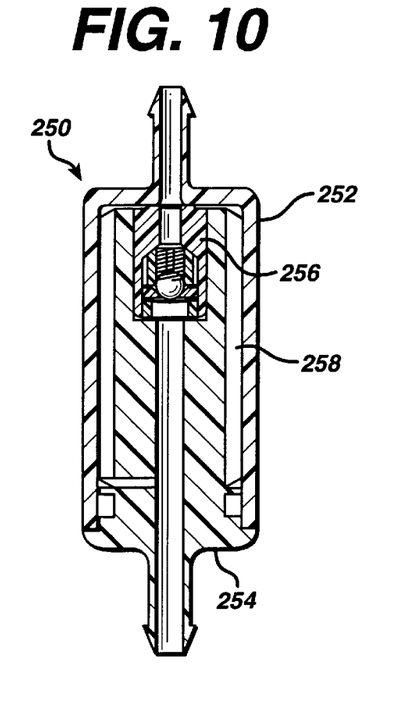
FIG. 10 is a cross-sectional view of a further alternate embodiment of a fluid flow limiting device in accordance with the invention.

It will be appreciated by those of ordinary skill in the art that the particular structure and arrangement of the device 10 is illustrative only and may be varied without departing from the spirit of the invention. For example, the substantially helical, axially bidirectional secondary passage 40 of the device 10 may be modified in order to tailor the desired fluid flow rate reduction. As examples, the number and size of the threads defining the channels 60, 62 of the secondary passage may be modified. Also, the pitch of the threads 48, 50 may be modified and/or the slot 56 leading to the secondary passage 40 may be modified in size and/or number. Further, structures other than helical vanes, or threads may be provided in the secondary passage 40 and/or the threads may be alternated with one or more regions without threads in order to introduce a desired fluid flow rate reduction. Additionally, fluid flow schemes other than axially bidirectional may be implemented to provide either the primary and/or secondary passages. For example, the secondary passage may comprise only the channel 60, with the fluid entering the body channel 24 at the distal end of channel 60 (i.e., rather than entering channel 62.) Such an arrangement, as shown in the embodiments of FIGS. 8 and 10, may be characterized as axially unidirectional. As a further alternative, a circumferentially bidirectional fluid flow scheme may be implemented in which the fluid flows at least partially around the circumference of the device in a first direction then axially, and then at least partially around the circumference of the device in a second, opposite direction.

Referring to FIG. 8, an alternate embodiment of a fluid flow limiting device 200 includes a housing 202, a body 204, a detector 208 and a flow reducing element in the form of a screw element 206, each of which is substantially identical to respective elements 14, 16 and 46 of the device 10 of FIGS. 2 and 3. Thus, device 200 includes a primary passage 236 formed by a channel 230 (FIG. 9) through the detector 208 and a substantially axially aligned channel through the body 204 and a secondary passage 240 formed by the screw element 206 and body 204.

The device 200 differs from the device 10 of FIGS. 2 and 3 in that the device 200 is separate from the shunt system valve and is suitable for placement as illustrated in FIG. 1A. To this end, the device 200 includes an inlet connector 210 adapted for mating with a brain ventricle catheter 21 (FIG. 1A) and an outlet connector 215 adapted for mating with the drainage catheter 23 (FIG. 1A). Further, the secondary passage 240 can be characterized as axially unidirectional. Device 200 further includes a slightly modified detector 208 in order to accommodate the inlet connector 210.

Figure 9:
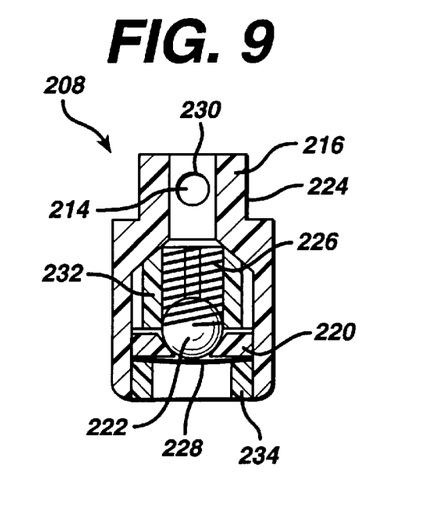
FIG. 9 is an enlarged cross-sectional view of the detector of the fluid flow limiting device of FIG. 8.

Referring also to the expanded view of the detector 208 in FIG. 9, the detector 208 includes a housing 216 in which a seat 220, a spherical ball 222, a coil spring 226 and a flat spring 228 are positioned, each of which is substantially identical to respective components 104, 110, 112 and 114 of the device 10 of FIGS. 2 and 3. The housing 216 includes a neck 224 which is tapered to mate with the inlet connector 210 so that, in assembly, a channel 230 through the detector 208 is aligned with the input connector 210. The detector 208 includes an aperture 214 which permits fluid to flow from the inlet connector 210 into the secondary passage 240. A guide 232 is positioned to maintain axial alignment of the spring 226 and the ball 222 and a fixation ring 234 maintains the flat spring 228 pressed against the detector seat 220.

Referring to FIG. 10, a further alternative fluid flow limiting device 250 is shown. Like the above-described devices 10 and 200, the device 250 includes a housing 252, a body 254, a detector 256 and a flow reducing element in the form of a screw element 258. This embodiment differs from that of FIG. 8 in that the length of the screw element 258 is increased. Increasing the length of the screw element 258 illustrates one way to increase the extent to which the flow rate is reduced when the fluid flows through the secondary passage defined by the screw element 258.

Figure 10A:
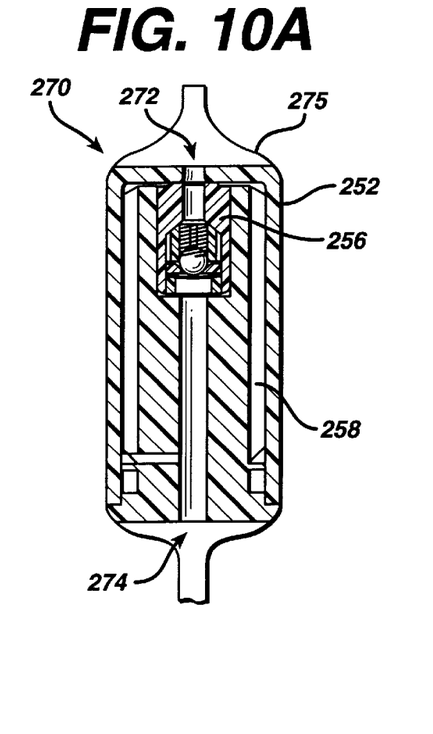
FIG. 10A is a cross-sectional view of a slightly modified version of the fluid flow limiting device of FIG. 10.

Referring also to FIG. 10A, in which like numbers refer to like elements, a further alternate embodiment 270 differs from device 250 of FIG. 10 only in that the inlet 272 and outlet 274 are in the form of apertures. That is, flow limiting device 270 does not include inlet and/or outlet connectors as shown in FIGS. 8 and 10. The device 270 illustrates a further alternative scheme for placement relative to a fluid shunt system. Specifically, the device 270 is suitable for placement within a catheter tube 275, as shown.

Figure 11:
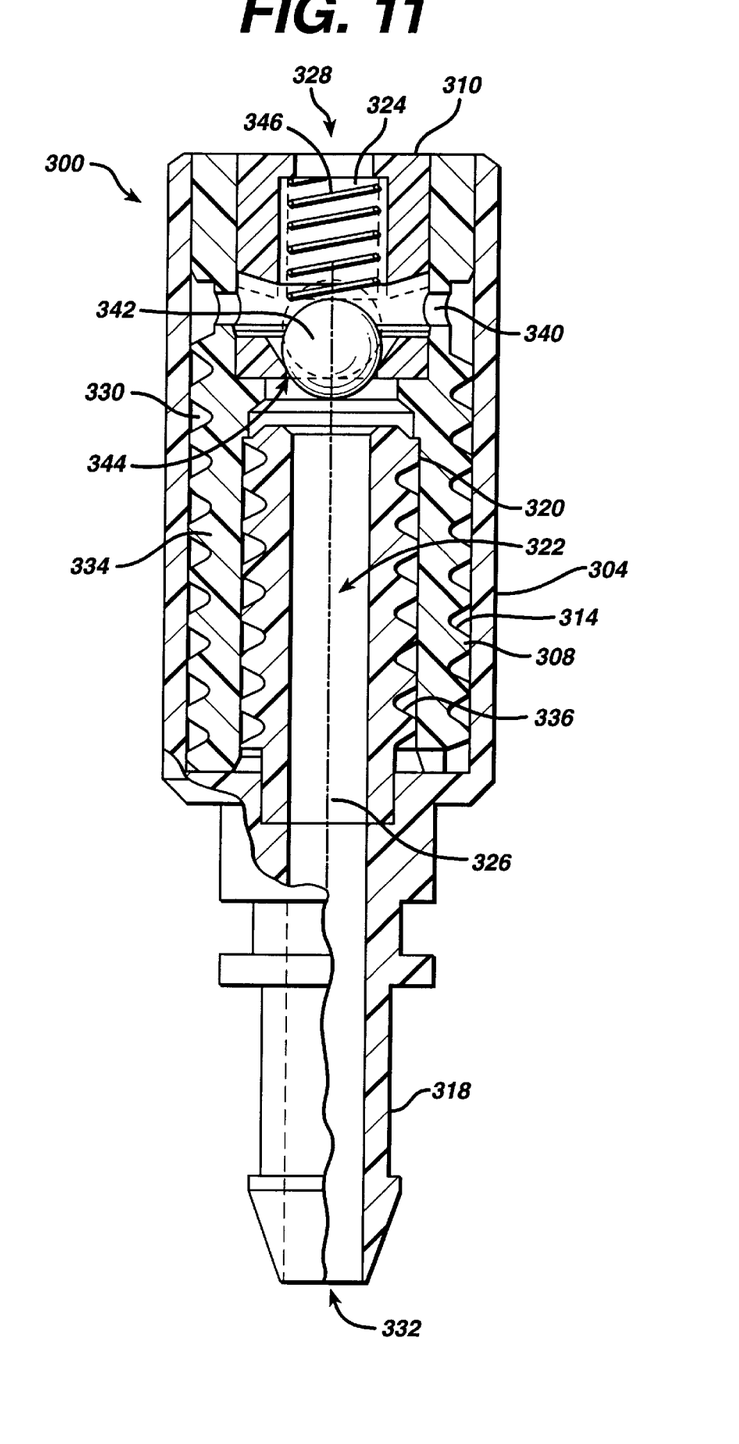
FIG. 11 is a cross-sectional view of another alternate embodiment of a fluid flow limiting device in accordance with the invention.

Referring to FIG. 11, an alternate fluid flow limiting device 300 includes a housing 304, a device body 308, a detector 310 and a flow reducing element in the form of a screw element 314. The overall operation of device 300 is similar to device 10 described above in conjunction with FIGS. 2 and 3. More particularly, the device 300 has a primary passage 322 between the inlet 328 and the outlet 332 which is formed by a channel 324 through the detector 310 and an axially aligned body channel 326. Further, a secondary passage 330 includes a first channel formed by screw threads 334 and a second channel formed by body threads 336 and thus, provides an axially bidirectional fluid flow path.

The device 300 differs from the device 10 (FIGS. 2 and 3) in several ways. First, the housing 304 of the device 300 is integral with the outlet connector 318, whereas, in the device 10, the outlet connector 70 is integral with the device body 16 and the housing 14 is a separate component. Further, the device 300 includes an aperture 340 between the detector 310 and the secondary passage 330, through which fluid enters the secondary passage. This arrangement is contrasted to the screw slot 56 (FIG. 3) through which fluid enters the secondary passage 40 of the device 10 and advantageously causes all of the fluid flow through the device 300 to be directed toward the closure element 342 of the detector 310.

Other differences between the fluid flow limiting device 300 and the device 10 are attributable to the design of the detector 310. Unlike the detector 30 (FIG. 3), the detector 310 does not include side portions which abut ledges 76 of the screw element 46 (FIG. 3) in assembly. Rather, in assembly, the detector 310 is seated within the body 308 and is prevented from moving further into the body by a combination of an interference fit with interior walls of the body 308 and ledges 320 of the body. Elimination of the side portions of the detector adjacent to screw element ledges 76 (FIG. 3) provides the device 300 with a smaller diameter than the device 10 and the body ledges 320 further permit the elimination of the fixation ring 118 (FIG. 3).

Finally, the device 300 permits use of an advantageous calibration technique by which a bias element 344 and a counterbias element 346 of the detector 310 are calibrated. In particular, during manufacture, a calibrating fluid, such as nitrogen, is directed through the device, from the inlet 328 to the outlet 332 328, while the detector 310 is pushed into the device body 308, toward the outlet, until a desired fluid flow reading is obtained.

Figure 12:
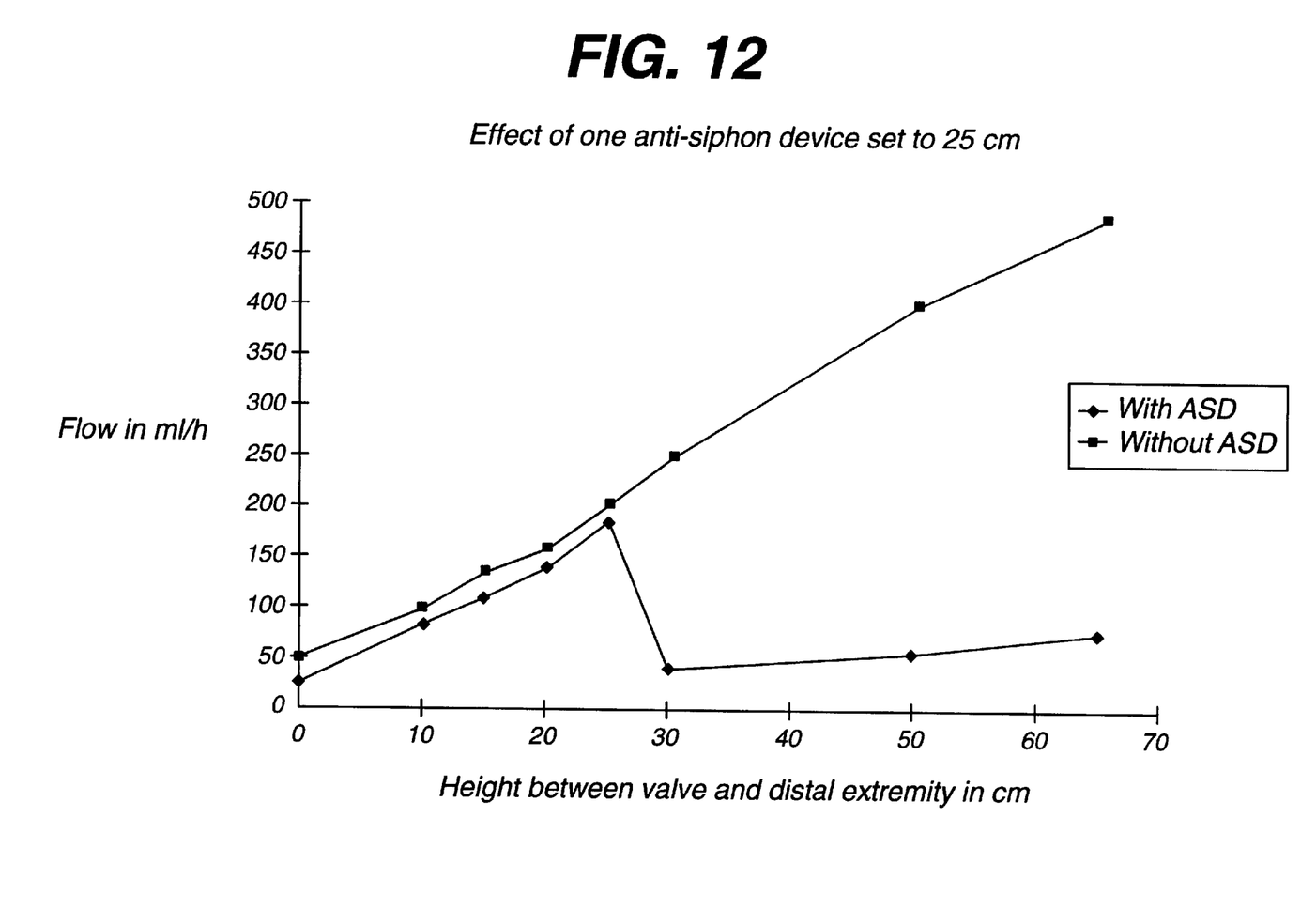
FIG. 12 is a graph illustrating the effect of use of a fluid flow limiting device according to the present invention.

Referring also to FIG. 12, a graph illustrates the effect of use of a fluid flow limiting device according to the invention. As is apparent, when the distance between the device and the region to which the fluid is directed (i.e., the distal extremity) exceeds approximately twenty-five centimeters, the fluid flow rate decreases significantly, thereby preventing overdrainage.

The foregoing description of the illustrative embodiments of the invention is presented to indicate the range of constructions to which the invention applies. Variations in the physical architecture and dimensions of the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. A device for limiting the flow of a fluid from a first region of a patient's body to a second region, comprising:
    a housing defining an inlet for receiving the fluid from the first region into the device;
    a device body defining an outlet for directing the fluid from the device to the second region, wherein at least a portion of the device body is disposed within the housing;
    a primary flow path disposed within the housing and in fluid communication with the inlet and the outlet for directing the fluid from the inlet to the outlet in response to the flow rate of the fluid being less than a predetermined level; and
    a secondary flow path disposed within the housing and in fluid communication with the inlet and the outlet for directing the fluid from the inlet to the outlet in response to the flow rate of the fluid being greater than or equal to the predetermined level, the secondary flow path being substantially tortuous and having a higher resistance to fluid flow than the primary path.

2. The device of claim 1 wherein the primary flow path extends substantially linearly between the inlet and the outlet.

3. The device of claim 2 wherein the secondary flow path is disposed concentrically around at least a portion of the primary flow path.

4. The device of claim 1 wherein the secondary flow path has a length greater than that of the primary flow path.

5. The device of claim 1 further comprising a detector disposed in the primary flow path, said detector being operative to close the primary flow path when the flow rate of the fluid is greater than or equal to the predetermined level.

6. The device of claim 5 wherein the detector comprises:
    a detector seat having an aperture;
    a closure element adapted for movement between a closed position in abutment with the detector seat in which the primary flow path is closed and an open position in spaced relation with the detector seat in which the primary flow path is open;
    a bias element for biasing the closure element into spaced relation with the detector seat; and
    a counterbias element for biasing the closure element into abutment with the detector seat.

7. The device of claim 6 wherein the bias element and the counterbias element are springs.

8. A fluid flow limiting device for limiting flow from a first region of a patient's body to a second region, comprising:
    a housing defining an inlet for receiving a fluid from the first region of the patient's body into the device;
    a body disposed at least partially within the housing and having a body channel terminating at an outlet for directing the fluid from the device;
    a detector disposed between the inlet and the body channel and having a detector channel in substantial axial alignment with the body channel, wherein the detector channel and the body channel form a primary flow path for fluid flow from the inlet to the outlet in response to a fluid flow rate being less than a predetermined level; and
    a flow reducing element disposed between the body and the housing and forming a substantially tortuous secondary flow path for fluid flow from the inlet to the outlet in response to a fluid flow rate being greater than the predetermined level, wherein the secondary flow path has a higher resistance to fluid flow than the primary flow path.

9. The fluid flow limiting device of claim 8 wherein the flow reducing element comprises a helical passageway.

10. The fluid flow limiting device of claim 9 wherein the helical passageway is formed by a screw element having external threads which define a first channel of the secondary flow path and wherein the body has external threads which define a second channel of the secondary flow path.

11. The fluid flow limiting device of claim 10 wherein the detector further comprises:
    a detector seat having an aperture;
    a closure element adapted for movement between a closed position in abutment with the detector seat in which the primary flow path is closed and an open position in spaced relation with the detector seat in which the primary flow path is open;
    a bias element for biasing the closure element into spaced relation with the detector seat; and
    a counterbias element for biasing the closure element into abutment with the detector seat.

12. A device for limiting the flow of a fluid from a first region of a patient's body to a second region, comprising:
- a housing defining an inlet for receiving the fluid from the first region into the device;
- a device body defining an outlet for directing the fluid from the device to the second region, wherein at least a portion of the device body is disposed within the housing;
- a primary flow path disposed within the housing and in fluid communication with the inlet and the outlet for directing the fluid from the inlet to the outlet in response to the flow rate of the fluid being less than a predetermined level; and a secondary flow path disposed within the housing and in fluid communication with the inlet and the outlet for directing the fluid from the inlet to the outlet in response to the flow rate of the fluid being greater than or equal to the predetermined level, wherein at least a portion of the secondary flow path is substantially helical.

* * * * *